US012807550B2

(12) United States Patent
Hwang et al.

(10) Patent No.: US 12,807,550 B2
(45) Date of Patent: Nov. 24, 2026

(54) METHOD FOR PREPARING ISOPROPYL ALCOHOL

(71) Applicant: LG CHEM, LTD., Seoul (KR)

(72) Inventors: Sung June Hwang, Daejeon (KR); Sung Kyu Lee, Daejeon (KR); Kyung Soo Jang, Daejeon (KR); Kil Taek Lim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 426 days.

(21) Appl. No.: 18/711,533

(22) PCT Filed: May 25, 2023

(86) PCT No.: PCT/KR2023/007144

§ 371 (c)(1),
(2) Date: May 17, 2024

(87) PCT Pub. No.: WO2024/043443

PCT Pub. Date: Feb. 29, 2024

(65) Prior Publication Data

US 2025/0026701 A1 Jan. 23, 2025

(30) Foreign Application Priority Data

Aug. 22, 2022 (KR) ........................ 10-2022-0104769
Apr. 24, 2023 (KR) ........................ 10-2023-0053289

(51) Int. Cl.

| | |
|---|---|
| ***C07C 29/04*** | (2006.01) |
| ***C07C 29/80*** | (2006.01) |
| ***C07C 29/84*** | (2006.01) |

(52) U.S. Cl.
CPC .............. *C07C 29/04* (2013.01); *C07C 29/80* (2013.01); *C07C 29/84* (2013.01)

(58) Field of Classification Search
None
See application file for complete search history.

(56) References Cited

U.S. PATENT DOCUMENTS 3,989,762 A 11/1976 Ester

FOREIGN PATENT DOCUMENTS

EP 2939995 A1 * 11/2015 ............ C07C 29/04
JP 2003-535836 A 12/2003

(Continued)

*Primary Examiner* — Amy C Bonaparte

(74) *Attorney, Agent, or Firm* — Bryan Cave Leighton Paisner LLP

(57) ABSTRACT

A method for preparing isopropyl alcohol is provided. The method includes passing reaction water through a first heat exchanger and a second heat exchanger to heat the reaction water, supplying the reaction water having passed through the second heat exchanger to a reactor as a feed stream with a propylene monomer to produce a gaseous reaction product including isopropyl alcohol (IPA), purifying isopropyl alcohol from the gaseous reaction product and recovering process water, and passing the process water through the second heat exchanger to cool the process water, and transferring a portion of the cooled process water to the first heat exchanger, wherein the reaction water is brought into contact with the portion of the cooled process water in the first heat exchanger for primary heating, and then brought into contact with the process water in the second heat exchanger for secondary heating.

11 Claims, 1 Drawing Sheet

(56) References Cited

FOREIGN PATENT DOCUMENTS

| | | | |
|---|---|---|---|
| JP | 2010-083825 | A | 4/2010 |
| JP | 6823666 | B2 | 2/2021 |
| KR | 10-0219006 | B1 | 9/1999 |
| KR | 10-2004-0055805 | A | 6/2004 |
| KR | 10-2014-0032331 | A | 3/2014 |
| KR | 10-1662896 | B1 | 10/2016 |
| KR | 10-2019-0019060 | A | 2/2019 |
| KR | 10-2020-0065579 | A | 6/2020 |
| KR | 10-2021-0035735 | A | 4/2021 |
| KR | 10-2021-0158146 | A | 12/2021 |

* cited by examiner

【FIG. 1】
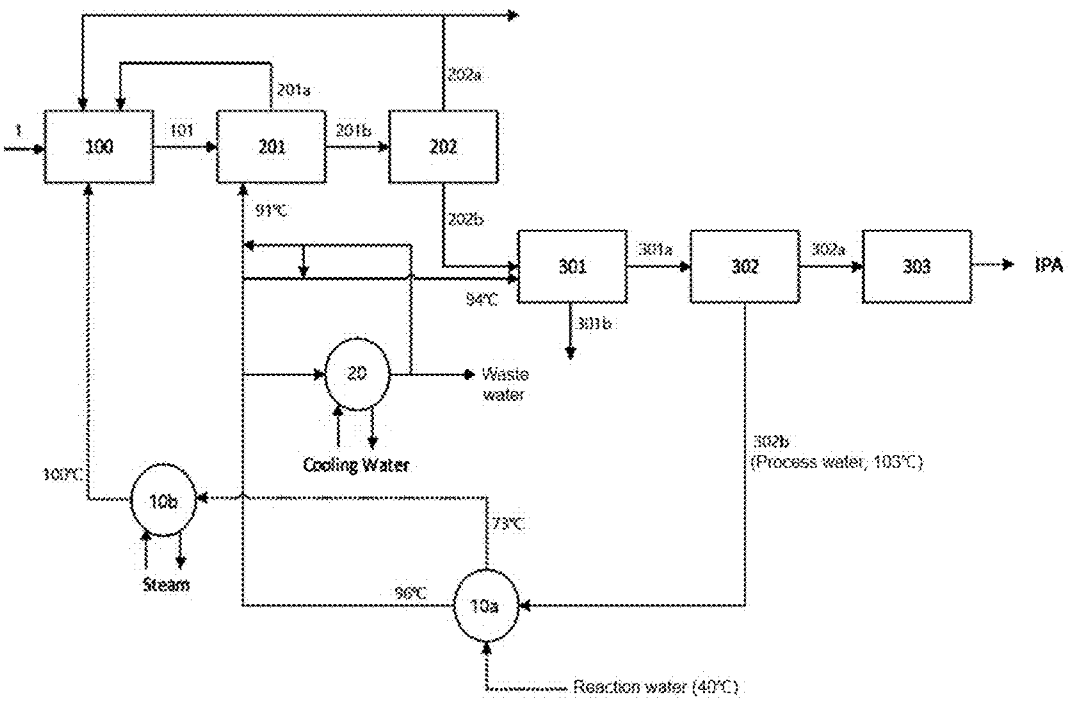
Related Art
【FIG. 2】
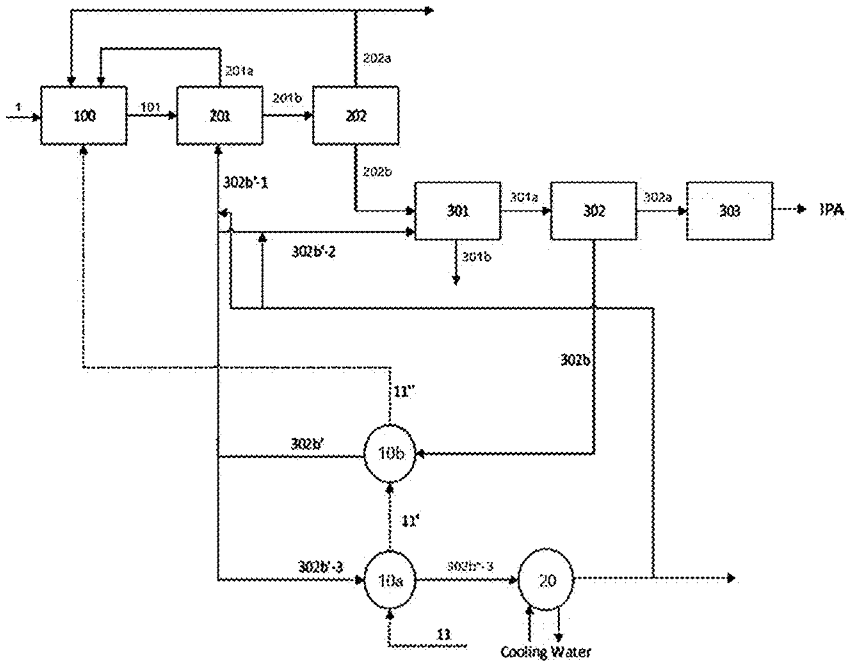

METHOD FOR PREPARING ISOPROPYL ALCOHOL

CROSS-REFERENCE TO RELATED APPLICATIONS

This application is a National Stage Application of International Application No. PCT/KR2023/007144 filed on May 25, 2023, and claims the benefit of priorities to Korean Patent Application No. 10-2022-0104769, filed on Aug. 22, 2022, and Korean Patent Application No. 10-2023-0053289, filed on Apr. 24, 2023, the disclosures of which are incorporated herein by reference in their entirety.

FIELD

The present disclosure relates to a method for preparing isopropyl alcohol.

BACKGROUND

Isopropyl alcohol (IPA) is used for various purposes including a solvent for cleaning agents, raw materials for industrial paints and reagents, paints, inks, and the like in the electronics industry such as manufacture of semiconductor or liquid crystal display (LCD).

Isopropyl alcohol may be prepared by reacting propylene and water. For example, a propylene monomer and water are reacted in a gas phase in a reaction unit to obtain a reaction product including isopropyl alcohol, an unreacted propylene monomer, unreacted water, and by-products, and the gaseous reaction product passes through a later process column to separate the propylene monomer, water, and the by-product, thereby purifying isopropyl alcohol.

In this process, water used as the reaction water (40 °C) is heated to a target temperature (100 °C) and then supplied in a reactor, and is reacted with propylene to produce isopropyl alcohol, and unreacted water may be separated in an isopropyl alcohol purification unit, cooled, and recycled to two types of process water which may be used for washing an absorption column and an organic substance (hydrocarbon) removal column, and a portion of the unreacted water is discharged as waste water. The reaction water supplied in the reactor needs to be heated to 100 °C, and process water recovered through the reactor needs to be cooled for recycling into wash water.

Thus, conventionally, heat exchange of reaction water of 40 °C. with process water (103 °C) which is recovered through a process of purifying isopropyl alcohol was performed. Herein, in order for the process water to be recycled to an absorption column and an organic substance removal column, a temperature of 96 °C should be maintained, and thus, an amount of heat transferred by the heat exchange with the process water is limited, so that the reaction water is preheated to only about 73 °C. Therefore, in order for the reaction water to be heated to a target temperature (100 °C), a hot utility such as steam or steam condensate is needed. In addition, in order for the process water cooled to 96 °C by the heat exchange to be used for washing the absorption column and the organic substance removal column, the process water is mixed with waste water of a low temperature, and then adjusted to process water of 91 °C and process water of 94 °C and recycled, and a portion thereof is discharged as waste water.

FIG. 1 schematically shows a process of heating reaction water before supplying the reaction water to a reactor in a conventional process of preparing IPA.

Referring to FIG. 1, a gaseous reaction product obtained in a reactor 100 passes through an absorption column 201, a gas purification unit 202, an organic substance removal column 301, a water removal column 302, and an IPA separation unit 303 to obtain purified IPA, and in order to use water of 103 °C recovered from a lower portion of the water removal column 302 as process water, the water is heat exchanged with reaction water of 40 °C in a first heat exchanger 10*a*, and then the reaction water preheated to 73 °C by the heat exchange is supplied in a second heat exchanger 10*b*, heated to a target temperature (100 °C) using a heating means (for example, low-pressure steam or low-pressure steam condensate of 140 °C to 200 °C), and supplied in the reactor 100. Meanwhile, the process water of 103 °C is cooled to 96 °C by heat exchange with the reaction water of 40 °C, and a portion thereof is transferred to an absorption column 201 and an organic substance removal column 301, respectively, and used as wash water and the remaining is discharged as waste water. That is, the process water may be heat exchanged with cooling water in a cooler 20 and discharged as waste water of a low temperature, and a portion of the waste water of a low temperature may be used for adjusting the process water of 96 °C to process water of 91 °C and process water of 94 °C.

When a separate heating means such as steam of high temperature is used for heating the reaction water as such, energy consumption is increased, and in order to perform heat exchange of all process water having a high flow rate with reaction water, the heat exchanger should have a large area, and thus, there is limitation of increased cost of process design. In addition, when process water which has been heat exchanged with the reaction water is discharged as waste water, an amount of heat required for waste cooling may be large.

SUMMARY

The present disclosure is to solve the problems mentioned in the Background Art, and an object of the present disclosure is to provide a method which may minimize energy consumption and a rise in cost by heating reaction water used for preparing isopropyl alcohol to a target temperature only by heat exchange without a separate heating means and supply the heated reaction water to a reactor.

According to one aspect of the present disclosure to solve the above mentioned problems, a method for preparing isopropyl alcohol includes:

(S1) passing reaction water through a first heat exchanger and a second heat exchanger to heat the reaction water, (S2) supplying the reaction water having passed through the second heat exchanger to a reactor as a feed stream with a propylene monomer to produce a gaseous reaction product including isopropyl alcohol (IPA), (S3) purifying isopropyl alcohol from the gaseous reaction product and recovering process water, and (S4) passing the process water through the second heat exchanger to cool the process water, and transferring a portion of the cooled process water to the first heat exchanger, wherein the reaction water is brought into contact with the portion of the cooled process water in the first heat exchanger for primary heating, and then brought into contact with the process water in the second heat exchanger for secondary heating.

According to the present disclosure, reaction water supplied in a reactor for preparing isopropyl alcohol is primarily heated by heat exchange with a cooled stream of process water recovered through a later process after the reactor, and then secondary heated by subsequent heat exchange with process water which is higher than the cooled stream, thereby being raised to a target temperature without a separate heating means.

In addition, a limitation of heat exchange of primarily heated reaction water with process water having a high flow rate may be overcome and a cooling means required for waste water cooling may be reduced, which is thus advantageous in terms of energy consumption and costs.

BRIEF DESCRIPTION OF DRAWINGS

FIG. 1 shows a process of heating reaction water before supplying the reaction water to a reactor in a conventional process of preparing IPA.

FIG. 2 shows a process of heating reaction water before supplying the reaction water to a reactor in a method for preparing IPA according to an exemplary embodiment of the present disclosure.

DETAILED DESCRIPTION

The terms and words used in the description and claims of the present disclosure are not to be construed limitedly as having general or dictionary meanings but are to be construed as having meanings and concepts meeting the technical ideas of the present disclosure, based on a principle that the inventors are able to appropriately define the concepts of terms in order to describe their own inventions in the best mode.

The meaning of "comprising" or "containing" used herein embodies specific characteristics, domains, integers, steps, actions, elements, or components, and does not exclude the addition of other specific characteristics, domains, integers, steps, actions, elements, or components.

The term "stream" used herein may refer to a fluid flow in a process, or may refer to a fluid itself flowing in a pipe. Specifically, the stream may refer to both a fluid itself flowing in a pipe connecting each device and a fluid flow. In addition, the fluid may include any one or more components of gas, liquid, and solid.

An exemplary embodiment of the present disclosure relates to a method for preparing isopropyl alcohol (IPA) including: (S1) passing reaction water through a first heat exchanger and a second heat exchanger to heat the reaction water, (S2) supplying the reaction water having passed through the second heat exchanger to a reactor as a feed stream with a propylene monomer to produce a gaseous reaction product including isopropyl alcohol (IPA), (S3) purifying isopropyl alcohol from the gaseous reaction product and recovering process water, and passing the process water through the second heat (S4) exchanger to cool the process water, and transferring a portion of the cooled process water to the first heat exchanger, wherein the reaction water is brought into contact with the portion of the cooled process water in the first heat exchanger for primary heating, and then brought into contact with the process water in the secondary heat exchanger for secondary heating.

FIG. 2 illustrates the method for preparing isopropyl alcohol according to an exemplary embodiment of the present disclosure, in which isopropyl alcohol may be prepared using a system including a first heat exchanger 10*a*, a second heat exchanger 10*b*, a cooler 20, a reactor 100, an absorption column 201, a gas purification unit 202, an organic substance removal column 301, a water removal column 302, and an IPA separation unit 303.

Usually, water used as a raw material for preparing isopropyl alcohol, that is, reaction water is supplied in a reactor after being heated from an initial temperature of 30 to 50 °C (for example, 40 °C) to a target temperature of at least 100 °C for a gas phase reaction with propylene. The present disclosure is characterized by heating to a target temperature by performing second heat exchange using process water recovered in a later process column before supplying reaction water to a reactor 100.

Referring to FIG. 2, in the present disclosure, reaction water 11 is primarily heated by heat exchange by contact with a portion 302*b*'-3 of a cooled stream 302*b*' of process water which is recovered through a later process column in a first heat exchanger 10*a*, and the primarily heated stream 11' is secondarily heated by subsequent heat exchange by contact with a process water stream 302*b* higher than the cooled stream in a second heat exchanger 10*b* to obtain secondarily heated reaction water 11", which is supplied in the reactor 100.

The process water may include unreacted water and wash water which are recovered from a process of purifying isopropyl alcohol by passing the gaseous reaction product through later process columns such as the absorption column, the organic substance removal column, the water removal column, and the like, which are applied for separating unreacted propylene monomer, by-products, and the like. Since the recovered process water is a stream discharged in a lower portion of a water removal column 302, it is in a high temperature state of 103 to 110 °C, for example, 105 to 107 °C, and thus, cooling is needed for recycle again.

As illustrated in FIG. 2, process water 302*b* recovered in a latter process column may be cooled to 98 to 104 °C, for example, 100 to 104 °C by passing the process water through the second heat exchanger 10*b*. Only when the cooling temperature range is satisfied, an optimal temperature range may be maintained in a process of adjusting a temperature using waste water for washing of a later process column. The waste water is discharged through the heat exchanger 10*a*, and, if necessary, an additional cooler 20. For example, process water 302*b*' which is passed through the heat exchanger 10*b* and cooled to a temperature of 98 to 104 °C diverges and is used as wash water 302*b*'-1 of an absorption column 201 and wash water 302*b*'-2 of an organic substance removal column 301, and at this time, it is mixed with waste water to maintain a temperature appropriate for the wash water, that is, a optimal temperature (90 to 92 °C) for washing the absorption column 201 and an optical temperature (94 to 96 °C) for washing the organic substance removal column 301.

In addition, another portion 302*b*'-3 of the cooled process water may be used for heat exchange of the reaction water. Specifically, a portion of the stream 302*b*'-3 of the cooled process water may be heat exchanged by contact with the water 11 in the first heat exchanger 10*a*, and a reaction reaction water stream 11' passed through the first heat exchanger is primarily heated to show a temperature of 80 to 95 °C, for example, 90 to 92 °C Meanwhile, a portion of the stream 302*b*'-3 of the cooled process water may be passed through the first heat exchanger 10*a* to be secondarily cooled to 40 to 70 °C.

In an exemplary embodiment of the present disclosure, a flow ratio by weight (wt/wt) between the reaction water 11 and the cooled process water 302*b*'-3 which are passed through the first heat exchanger 10*a* may be 1:1 to 1:1.7, for example, 1:2 to 1:1.6, and when the flow ratio range is satisfied, the size of the second heat exchanger 10*b* may be decreased while the reaction water is heated to a target temperature (for example, 80 to 95 °C), and the heat transfer dedicated area of the first heat exchanger 10*a* may be designed optimally.

The process water 302*b*"-3 which is secondarily cooled by passing it through the first heat exchanger 10*a* may be treated as waste water, and, if necessary, it is passed through an additional cooler 20 and diverges, and a portion thereof may be used for adjusting the temperature of the wash water and the remaining may be discharged as waste water.

Subsequently, the primarily heated reaction water is brought into contact with a process water stream 302*b* of a high temperature in the second heat exchanger 10*b* and may be secondarily heated to 95 to 100°, for example, 98 to 100 °C.

In an exemplary embodiment of the present disclosure, a flow ratio by weight (wt/wt) between the primarily heated reaction water 11' and the process water 302*b* which are passed through the second heat exchanger may be 1:4 to 1:8, for example, 1:4 to 1:6, and when the flow ratio range is satisfied, sufficient wash water may be supplied in the absorption column and the organic substance removal column while the reaction water is heated to a target temperature (100 °C), and excessive energy consumption in the IPA separation unit may be prevented.

The secondarily heated reaction water stream 11" is supplied in the reactor 100 and reacted with propylene 1 in a gas phase to obtain a reaction product 101 including isopropyl alcohol.

Since only a portion of the propylene used as a raw material is used in the reaction, the reaction product may include 65 to 85 wt % of an unreacted propylene monomer, 4 to 8 wt % of isopropyl alcohol, and 5 to 30 wt % of water. In addition, the reaction product may further include other by-products, for example, high boiling point organic substance such as isopropyl ether (DIPE) and hexene, acetone, and n-propyl alcohol (NPA). Therefore, a later process column for purifying isopropyl alcohol from the reaction product is performed.

First, a gaseous reaction product 101 is supplied in an absorption column 201 and brought into contact with wash water to obtain an aqueous solution 201*b* including isopropyl alcohol. As described above, as the wash water of the absorption column 201, a portion 302*b*'-1 of the stream 302*b*' cooled by passing the process water 302*b* recovered from the water removal column 302 in the later step through the second heat exchanger 10*b* may be used.

Specifically, the reaction product 101 may be supplied in the lower stage of the absorption column 201 and the wash water may be supplied in the upper stage of the absorption column 201, and gaseous isopropyl alcohol is absorbed by the wash water and obtained in a lower liquid stream 201*b*, and a gaseous stream 201*a* including an unreacted propylene monomer is separated in the upper portion and recovered to the reactor 100.

The lower liquid stream of the absorption column 201 may include the unreacted propylene monomer in a small amount, for example, 5 wt % or less or 2 to 5 wt %, in addition to isopropyl alcohol and unreacted water.

According to an exemplary embodiment of the present disclosure, the flow rate of the wash water supplied in the absorption column 201 may be 15 to 40 wt % or 15 to 35 wt % of the flow rate of the reaction product. When the wash water is supplied in the flow rate within the range, excessively increased energy expense for recovering the wash water in the later step may be prevented, while absorbency of isopropyl alcohol included in the reaction product is improved.

The absorption column 201 may be operated at a temperature of 90 to 100 °C or 90 to 95 °C and a pressure of 25 to 40 kg/cm$^2$·g or 25 to 35 kg/cm$^2$·g. When the operation conditions are satisfied, an upper discharge stream including the unreacted propylene monomer and a lower discharge stream including isopropyl alcohol may be effectively separated.

A liquid 201*b* stream including isopropyl alcohol separated from the absorption column 201 may be supplied in a gas purification unit 202 and separated into an upper stream 202*a* including low-boiling point components and a lower stream 202*b* including isopropyl alcohol, water, and by-products.

The upper stream 202*a* including low-boiling point components separated in the gas purification unit may include an unreacted propylene monomer and inert gas (for example, ethane or propane).

The lower stream 202*b* separated in the gas purification unit may include isopropyl alcohol, water, and by-products (for example, isopropyl ether (DIPE), hexene, n-propyl alcohol (NPA), and the like).

The gas purification unit 202 may include one or more flash drums and one or more gas purification columns. First, low-boiling point components are first separated in the flash drum and are supplied in the gas purification column again to separate the unreacted propylene monomer and the low-boiling point components of inert gas in the upper portion and a small amount of high-boiling point components in the lower portion.

The unreacted propylene monomer separated in the gas purification unit may be recovered to the reactor 100 and inert gas may diverge for exhaust.

Meanwhile, the lower stream 202*b* of the gas purification unit 202 is transferred to an IPA purification unit for recovering IPA.

First, the stream may be brought into contact with wash water in the organic substance removal column 301 and separated into a liquid phase 301*a* including isopropyl alcohol and water and a liquid phase 301*b* including organic substance. As described above, as the wash water of the organic substance removal column 301, a portion 302*b*-2 of the cooled stream after the process water 302*b* recovered from the water removal column 302 in the later step is passed through the second heat exchanger 10*b* may be used.

An alcohol component is dissolved by the wash water, and a liquid phase 301*a* including an alcohol component and water of the organic substance removal column 301 may be separated to the lower portion and the remaining organic liquid phase 301*b* may be removed in a connected condenser.

In an exemplary embodiment of the present disclosure, the flow rate of the wash water supplied in the organic substance removal column 301 may be 60 to 100 wt % or 65 to 95 wt % of the flow rate of the stream 202*b*. When the wash water is supplied in the flow rate within the range, excessively increased energy expense for recovering the wash water in the later step may be prevented, while absorbency of isopropyl alcohol included in the corresponding stream is improved.

The liquid phase 301*a* separated in the organic substance removal column 301 may include 3 to 10 wt % of isopropyl alcohol and 90 to 97 wt % of water. That is, since most of the liquid phase 301*a* includes the wash water, its separation is needed.

Therefore, the liquid phase 301_a_ which is separated in the organic substance removal column 301 and includes isopropyl alcohol and water is supplied in a water removal column 302, and separated into a stream 302_a_ including isopropyl alcohol in the upper portion and a lower stream 302_b_ of water.

The stream 302_a_ separated in the water removal column 302 includes an azeotrope of isopropyl alcohol and water, and for example, may include 80 to 90 wt % of isopropyl alcohol and 10 to 20 wt % of water.

Meanwhile, a water stream 302_b_ is recovered as a process water in the water removal column 302 and passed through the second heat exchanger 10_b_ to be cooled, and a portion thereof may be recycled as wash water and the remaining may be used for heat exchange of reaction water.

The water removal column 302 may be operated at a temperature of 70 to 150 °C or 80 to 140 °C and a pressure of 1 to 5 $kg/cm^2 \cdot g$ or 1 to 2 $kg/cm^2 \cdot g$. When the operation conditions are satisfied, the azeotrope of isopropyl alcohol and water may be effectively separated.

Thereafter, an azeotrope stream 302_a_ separated in the water removal column 302 is supplied in an IPA separation unit 303 including an IPA purification column and a solvent recovery column and IPA is recovered.

For example, when an organic solvent (for example, cyclohexane, benzene, and the like) is added to the IPA purification column of the IPA separation unit 303 as an azeotropic agent, azeotropy of isopropyl alcohol and water may be damaged to obtain highly purified isopropyl alcohol. In addition, a stream including an azeotropic agent and water is separated in the upper portion of the IPA purification column and then supplied in a solvent recovery column to separate the upper stream of the azeotropic agent and the lower stream of water, and the upper stream of the azeotropic agent may be refluxed to the IPA purification column.

In the present disclosure, if necessary, devices such as a distillation column, a condenser, a reboiler, a valve, a pump, a separator, and a mixer may be further used.

According to the present disclosure as described above, primary heating is performed by heat exchange of reaction water used for preparing isopropyl alcohol with a cooled stream of process water recovered through a later process column of a reactor, and secondary heating is performed by subsequent heat exchange with process water which is higher than the cooled stream, thereby achieving a target temperature rise without a separate heating means.

In addition, a limitation of heat exchange of primarily heated reaction water with process water having a high flow rate may be overcome and a cooling means required for waste water cooling may be reduced, which is thus advantageous in terms of energy consumption and costs.

EXAMPLES AND COMPARATIVE EXAMPLE

Hereinafter, the present disclosure will be described in more detail by the examples. However, the following examples are provided for illustrating the present disclosure, and it is apparent to a person skilled in the art that various modifications and alterations may be made without departing from the scope and spirit of the present disclosure and the scope of the present disclosure is not limited thereto.

Example 1

As shown in FIG. 2, isopropyl alcohol was prepared using a system including a first heat exchanger 10_a_, a second heat exchanger 10_b_, a cooler 20, a reactor 100, an absorption column 201, a gas purification unit 202, an organic substance removal column 301, a water removal column 302, and an IPA separation unit 303.

(Step 1) Heat Exchange of Reaction Water

Reaction water 11 of 40 °C and a portion 302_b_'-3 of a process water stream 302_b_' which was recovered in the water removal column 302 and then cooled to 103 °C through the second heat exchanger 10_b_ were passed through the first heat exchanger 10_a_, so that a reaction water stream 11' which was primarily heated to 91 °C and a process water stream 302_b_"-3 which was cooled to 62 °C outflowed. At this time, a flow ratio by weight between the reaction water 11 and the process water stream 302_b_'-3 which were passed through the first heat exchanger 10_a_ was adjusted to 1:1.2.

Subsequently, the reaction water stream 11' which was primarily heated to 91 °C and the process water stream 302_b_ of 105 °C which was recovered in the water removal column 302 were the second heat exchanger 10_b_, so that a passed through reaction water stream 11" which was secondarily heated to 100 °C and a process water stream 302_b_' which was cooled to 103 °C outflowed. At this time, a flow ratio by weight between the reaction water stream 11' and the process water stream 302_b_' which were passed through the second heat exchanger 10_b_ were adjusted to 1:5.5.

The reaction water stream 11" which was passed through the second heat exchanger 10_b_ and secondarily heated to 100 °C was supplied in the reactor 100.

Meanwhile, the process water 302_b_"-3 which was passed through the first heat exchanger 10_a_ and cooled to 101 °C was transferred to a cooler 20 for treating waste water and cooled to 40 °C by heat exchange with cooling water, and then was diverged so that a portion was used for temperature adjustment of wash water and the remaining was discharged as waste water.

(Step 2) Production of Reaction Product

Reaction water 11" of 100 °C and a propylene monomer 1 were reacted in a gaseous phase in the reactor 100, thereby obtaining a reaction product including isopropyl alcohol, an unreacted propylene monomer, water, and organic substance.

(Step 3) Purification of Isopropyl Alcohol and Recovery of Process Water

A reaction product 101 including isopropyl alcohol obtained in step 2 was supplied in the lower portion of the absorption column 201, and wash water was supplied in the upper portion of the absorption column 201. A stream 302_b_'-1 which was adjusted to 91 °C by mixing a portion of the stream 302_b_' which was passed through the second heat exchanger 10_b_ and cooled to 101 °C with waste water cooled to 40 °C in the cooler 20 was used as the wash water. A liquid stream 201_b_ in which gaseous isopropyl alcohol was absorbed was discharged to the lower portion in the absorption column 201, and the gaseous stream 201_a_ including an unreacted propylene monomer was separated to the upper portion and recovered to the reactor 100.

The liquid stream 201_b_ in which isopropyl alcohol was absorbed was passed through a gas purification unit 202 to separate an upper stream 202_a_ having a low boiling point and a lower stream 202_b_ including isopropyl alcohol, water, and by-products, and then the lower stream 202_b_ was transferred to an organic substance removal column 301.

A stream 302_b_'-2 which was a portion of a stream 302_b_' which was passed through the second heat exchanger 10_b_ and cooled to 101 °C and was adjusted to 95 °C by mixing with waste water cooled to 40 °C was supplied in the upper portion of the organic substance removal column 301 as wash water, and a liquid phase 301_a_ including isopropyl alcohol and water and the remaining organic liquid phase 301*b* were separated by liquid-liquid separation.

The liquid phase 301*a* including isopropyl alcohol and water was supplied in a water removal column 302, and a stream 302*a* including isopropyl alcohol in the upper portion and a lower stream 302*b* of water were separated in the water removal column 302. The stream 302*a* including isopropyl alcohol was supplied in an IPA separation unit 303 to recover IPA.

(Step 4) Treatment of Recovered Process Water

The stream 302*b* which was separated in the lower portion of the water removal column 302 was process water of a high temperature of 105 °C and cooled to 103 °C in the second heat exchanger 10*b* as described above, and a portion of the process water cooled to 103 °C was transferred to the first heat exchanger 10*a* and used for heating the reaction water 11 and the remaining was used as wash water.

Example 2

The process was performed in the same manner as in Example 1, except that in step 1, the flow ratio between the reaction water 11 and the process water stream 302*b*'-3 was adjusted to 1:2.5 in the first heat exchanger 10*a*.

Comparative Example 1

(Step 1) Heat Exchange of Reaction Water

As shown in FIG. 1, reaction water of 40 °C and process water of 103 °C recovered in the lower portion of the water removal column 302 were heat exchanged in the first heat exchanger 10*a*, so that the reaction water which was primarily heated to 73 °C and the process water which was cooled to 96 °C outflowed.

The primarily heated reaction water was secondarily heated to 100 °C by supplying steam in the second heat exchanger 10*b*.

Meanwhile, the process water, which was passed through the first heat exchanger 10*a* to be cooled to 96 °C, diverged, and a portion was transferred to the absorption column 201 and the organic substance removal column 301 for use as wash water and the remaining was transferred to the cooler 20 for treating waste water and cooled to 40 °C by heat exchange with cooling water. A portion of the process water cooled to 30 °C was used for adjusting the temperature of the wash water and the remaining was discharged as waste water.

(Step 2) Production of Reaction Product

The reaction water which was secondarily heated to 100 °C was supplied in the reactor 100, and a reaction product including isopropyl alcohol was obtained by the same process as step 2 of Example 1.

(Step 3) Purification of Isopropyl Alcohol

The reaction product including isopropyl alcohol obtained in step 2 was subjected to the same purification process as step 3 of Example 1, thereby recovering isopropyl alcohol.

In Table 1, amounts of heat consumed to heat the reaction water and amounts of heat consumed to cool waste water in the examples and the comparative examples are compared.

TABLE 1

| | Method of heating reaction water | | Total amount of heat for heating[1)] | | Amount of heat for cooling waste water[2)] |
|---|---|---|---|---|---|
| | Primary heating | Secondary heating | Amount of steam used | Amount of heat exchange of process water | |
| Comparative Example 1 | Heat exchange of reaction water(40° C.) and process water (103° C.) | Heating primarily heated reaction water (73° C.) with steam | 0.45 | 0.55 | 1 |
| Example 1 | Heat exchange of reaction water(40° C.) and process water (103° C.) (flow ratio by weight 1:1.2) | Heat exchange of primarily heated reaction water (91° C.) and process water (105° C.) (flow ratio by weight 1:5.5) | 0 | 1 | 0.47 |
| Example 2 | Heat exchange of reaction water (40° C.) and process water (103° C.) (flow ratio by weight 1:2.5) | Heat exchange of primarily heated reaction water (91° C.) and process water (105° C.) (flow ratio by weight 1:5.5) | 0 | 1 | 4.09 |

[1)] A total amount of heat required for heating to 100° C. which was the final temperature of the reaction water was set to "1".

[2)] It is an amount of heat exchange using cooling water for treating waste water from process water, and is shown based on the amount of heat consumed in Comparative Example 1.

As shown in Table 1, in Comparative Example 1, since the amount of heat exchange using process water was 55% based on the total amount of heat required for heating reaction water, steam as an external heating means was used at 45% to cause energy consumption, but in Examples 1 and 2, since the total amount of heat required for heating reaction water used process water, a steam energy source was not used.

In particular, in Example 1, a flow ratio by weight between the reaction water 11 of 40 °C and the process water 302*b*'-3 of 103 °C which were passed through the first heat exchanger 10*a* during primary heating was adjusted to 1:1.2, thereby reducing an amount of cooling heat consumed for treating waste water from process water after heat exchange to 53% as compared with Comparative Example 1.

Meanwhile, in Example 2, the total amount of heat for heating reaction water was replaced with process water, but a flow ratio by weight of the process water 302*b*'-3 of 103 °C to the reaction water 11 of 40 °C was increased to 1:2.5 in the first heat exchanger 10*a*, and thus, the amount of heat for cooling waste water from process water was increased as compared with Comparative Example 1.

Therefore, considering the amount of heat for cooling waste water of process water in the heat exchange of the reaction water using the process water, it is preferred that the flow ratio by weight between the reaction water 11 of 40 °C and the process water 302*b*'-3 of 103 °C which are passed through the first heat exchanger 10*a* is adjusted to a predetermined range (for example, 1:1 to 1:1.7).

DESCRIPTION OF REFERENCE NUMERALS

1: Propylene raw material
10*a*, 10*b*: Heat exchanger
20: Cooler
11: Reaction water
11': Primarily heated reaction water
11": Secondarily heated reaction water
100: Reactor
101: Reaction product
201: Absorption column
201*a*, 201*b*: Discharge stream from absorption column
202: Gas purification unit
202*a*, 202*b*: Discharge stream from gas purification unit
301: Organic substance removal column
301*a*, 301*b*: Discharge stream from organic substance removal column
302: Water removal column
302*a*, 302*b*: Discharge stream from water removal column
303: IPA separation unit

The invention claimed is:

1. A method for preparing isopropyl alcohol, the method including:
(S1) passing reaction water through a first heat exchanger and a second heat exchanger to heat the reaction water,
(S2) supplying the reaction water having passed through the second heat exchanger to a reactor as a feed stream with a propylene monomer to produce a gaseous reaction product including isopropyl alcohol (IPA),
(S3) purifying isopropyl alcohol from the gaseous reaction product and recovering process water, and
(S4) passing the process water through the second heat exchanger to cool the process water, and transferring a portion of the cooled process water to the first heat exchanger,
wherein the reaction water is brought into contact with the portion of the cooled process water in the first heat exchanger for primary heating, and then brought into contact with the process water in the second heat exchanger for secondary heating.

2. The method for preparing isopropyl alcohol of claim 1, wherein the gaseous reaction product includes isopropyl alcohol, unreacted propylene, unreacted water, and by-products.

3. The method for preparing isopropyl alcohol of claim 1, wherein the step of (S3) includes:
supplying the gaseous reaction product in an absorption column and bringing the gaseous reaction product into contact with wash water to obtain an aqueous solution including isopropyl alcohol;
supplying the aqueous solution including isopropyl alcohol in a gas purification unit and separating the aqueous solution into an upper stream including low-boiling point components and a lower stream including isopropyl alcohol, water, and by-products;
supplying the lower stream of the gas purification unit in an organic substance removal column and bringing the stream into contact with wash water, thereby separating the stream into a liquid phase including isopropyl alcohol and water and a liquid phase including organic substance; and
supplying the liquid phase including isopropyl alcohol and water in a water removal column and separating the liquid phase including isopropyl alcohol and water into an upper stream including isopropyl alcohol and a lower stream of water, and then purifying isopropyl alcohol from the upper stream and recovering the lower stream as the process water.

4. The method for preparing isopropyl alcohol of claim 1, wherein the process water recovered in the step of (S3) has a temperature of 103 to 110 °C.

5. The method for preparing isopropyl alcohol of claim 1, wherein the process water recovered in the step of (S3) is passed through the second heat exchanger to be cooled to a temperature of 98 to 104 °C.

6. The method for preparing isopropyl alcohol of claim 1, wherein the process water cooled in the second heat exchanger is passed through the first heat exchanger to be secondarily cooled to 40 to 70 °C.

7. The method for preparing isopropyl alcohol of claim 1, wherein an initial temperature of the reaction water is 30 to 50 °C.

8. The method for preparing isopropyl alcohol of claim 1, wherein the reaction water is brought into contact with a portion of the cooled process water in the first heat exchanger to be primarily heated to a temperature of 80 to 95 °C.

9. The method for preparing isopropyl alcohol of claim 1, wherein the primarily heated reaction water is brought into contact with the process water in the second heat exchanger to be secondarily heated to a temperature of 95 to 100 °C.

10. The method for preparing isopropyl alcohol of claim 1, wherein a flow ratio by weight between the reaction water and the cooled process water which are passed through the first heat exchanger is 1:1 to 1:1.7.

11. The method for preparing isopropyl alcohol of claim 1, wherein a flow ratio by weight between the primarily heated reaction water and the process water which are passed through the second heat exchanger is 1:4 to 1:8.

* * * * *